United States Patent
Searcey et al.

(10) Patent No.: US 7,192,977 B2
(45) Date of Patent: Mar. 20, 2007

(54) BENZ-INDOLE AND BENZO-QUINOLINE DERIVATIVES AS PRODRUGS FOR TUMOR TREATMENT

(75) Inventors: Mark Searcey, London (GB); Laurence Hylton Patterson, London (GB)

(73) Assignee: School of Pharmacy, London (GB)

( * ) Notice: Subject to any disclaimer, the term of this patent is extended or adjusted under 35 U.S.C. 154(b) by 440 days.

(21) Appl. No.: 10/468,744

(22) PCT Filed: Feb. 22, 2002

(86) PCT No.: PCT/GB02/00801

§ 371 (c)(1), (2), (4) Date: Feb. 13, 2004

(87) PCT Pub. No.: WO02/067930

PCT Pub. Date: Sep. 6, 2002

(65) Prior Publication Data

US 2004/0138246 A1   Jul. 15, 2004

(30) Foreign Application Priority Data

Feb. 22, 2001   (EP) ................. 01301634

(51) Int. Cl.
| C07D 209/56 | (2006.01) |
| C07D 403/06 | (2006.01) |
| C07D 403/14 | (2006.01) |
| A61K 31/403 | (2006.01) |

(52) U.S. Cl. .................... 514/411; 548/427
(58) Field of Classification Search ......... 548/427; 514/411
See application file for complete search history.

(56) References Cited

U.S. PATENT DOCUMENTS

| 5,985,908 | A * | 11/1999 | Boger | 514/410 |
| 6,060,608 | A * | 5/2000 | Boger | 548/420 |
| 6,989,452 | B2 * | 1/2006 | Ng et al. | 548/429 |
| 7,087,600 | B2 * | 8/2006 | Ng et al. | 514/232.8 |
| 7,129,261 | B2 * | 10/2006 | Ng et al. | 514/411 |
| 2004/0157873 | A1 * | 8/2004 | Searcey et al. | 514/291 |
| 2004/0157880 | A1 * | 8/2004 | Searcey et al. | 514/311 |
| 2005/0026987 | A1 * | 2/2005 | Boger | 514/410 |
| 2006/0004081 | A1 * | 1/2006 | Chen et al. | 514/411 |

OTHER PUBLICATIONS

Dale L. Boger, et al., "Synthesis of CC-1065 and Duocarmycin Analogs via Intramolecular Aryl Radical Cyclization of a Tethered Vinyl Chloride," Tetrahdron Letters 39 (1998) pp. 2227-2230.

* cited by examiner

Primary Examiner—Fiona T. Powers
(74) Attorney, Agent, or Firm—Dickstein, Shapiro, LLP.

(57) ABSTRACT

Compounds of the general formula (I) or (IA) in which X is H, Y is a leaving group, $R^1$ preferably being an aromatic DNA binding subunit are prodrug analogues of duocarmycin. The compounds are expected to be hydroxylated at the carbon atom to which X is joined, by cytochrome P450, in particular by CYP1B1, expressed at high levels in tumors. The prodrug is expected to be activated preferentially in tumor cells, where it will act as a DNA alkylating agent preventing cell division

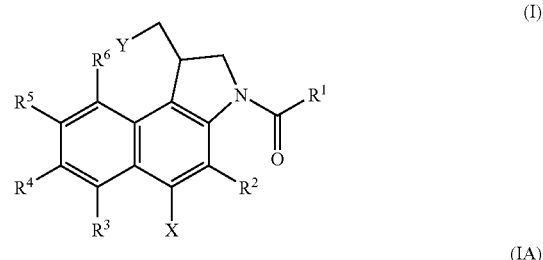

(I)

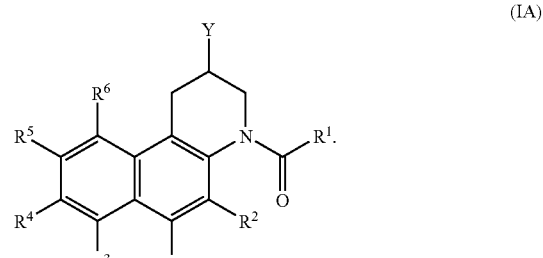

(IA)

59 Claims, No Drawings

BENZ-INDOLE AND BENZO-QUINOLINE DERIVATIVES AS PRODRUGS FOR TUMOR TREATMENT

The present invention concerns aromatic oxidation/hydroxylation activated prodrugs, particularly anti-tumour prodrugs and those which are specifically activated by the oxidation/hydroxylation activities of the cytochrome P450 family of enzymes.

Many conventional cytotoxic drugs are known that can be used for therapeutic purposes. However, they typically suffer from the problem that they are generally cytotoxic and therefore may affect cells other than those that are required to be destroyed. This can be alleviated to some extent by the use of targeted drug delivery systems, for example direct injection to a site of tumourous tissue or, e.g. binding the cytotoxic agent to an antibody that specifically recognises an antigen displayed only on the cancer cell surface. Alternatively, electromagnetic radiation may be used to cause chemical alteration in an agent at a desired site such that it becomes is cytotoxic. However, all of these techniques have, to a greater or lesser extent, certain limitations and disadvantages.

The compound (+)-CC-1065 and the duocarmycins are naturally occurring representatives of a class of DNA alkylating agents. The naturally occurring compounds consist of a DNA alkylating unit based upon a pyrrolo[3,2-e]indole core, with one or two sub units, conferring DNA binding capabilities. CC-1065 and duocarmycin A comprise a spirocyclic cyclopropane group responsible for the DNA alkylation properties. Duocarmycin $B_2$, $C_2$ and $D_2$ are believed to be precursors for cyclopropane actives, and comprise a substituted (by a leaving group) methyl group at the eight position on the dihydro pyrrole ring. CC-1065 has been synthesised by various routes, summarised by Boger et al in Chem. Rev. 1997, 97, 787–828.

In U.S. Pat. No. 4,413,132 the first synthesis of the left hand sub-unit of CC-1065 was described. The synthesis is based on a Winstein Ar-3' alkylation in which the cyclopropane ring is introduced. In a previous step, the A ring (of the indole core) is introduced by reaction of an aniline with an α-thiomethylester using chemistry based on Gassman's Oxindole Synthesis. The aniline has a protected phenolic hydroxyl group ortho to the $NH_2$ group, which, in the final product, is believed to be crucial for DNA alkylation. CC-1065 has broad antitumour activity but is too toxic against normal cells to be clinically useful.

Boger et al (1997) op.cit. also describe various deep-seated structural modifications of the DNA-alkylation subunit, in which the pyrrolo 'A' ring is replaced by other aromatic ring structures. In one class of analogues the replacement ring is a benzene ring.

Attempts have been made to target the delivery of CC-1065 and analogues by conjugating the drug via the DNA binding subunit to polymers, or specific binding agents such as antibodies or biotin described in U.S. Pat. No. 5,843,937. Boger et al in Synthesis 1999 SI, 1505–1509 described prodrugs of 1,2,9,9a-tetrahydrocyclopropa(c)benz[e]indol-4-one, in which the cyclopropane ring-opened version of the compounds were derivatised by reaction of the phenolic group to form esters and carbamates.

In Tet. Letts. (1998) 39, 2227–2230 Boger et al. describe (the synthesis of a range of precursors for the alkylation subunits of duocarmycin and CC-1065 analogues having a deep-seated structural modifications of the alkylation subunit. One of the compounds synthesised is a benzodihydroindole derivative:

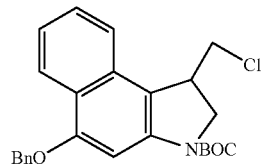

In J. Org. Chem. (2000), 65/13, 4101–4111 the corresponding ring closed indoline compound (CBI derivative) derived from that benzodihydroindole derivative was coupled to the DNA-binding subunit of CC-1065 and shown to have DNA alkylation activity. Analogues of the alkylation subunit precursor in which the benz moiety is substituted with methoxy or cyano were also synthesised. Similar compounds are described in WO-A-9745411 and WO-A-9732850. In '411 the benz moiety is substituted by cyano at the 7-position or the cyclopropane group may be difluoro substituted. In '850 the 7-methoxy CBI compounds are described.

In WO-A-9811101 the phenolic hydroxyl group in the B ring of CBI-type compounds is replaced by amino, nitro or thiol-based groups.

In J. Am. Chem. Soc. (1991), 113, 3980–3983 Boger et al describe a study to identify features of CC-1065 analogues contributing to the selectivity of the DNA-alkylation. The compounds tested in vitro had alkylating subunits based on 2,3-dihydroindole and included the 6-deshydroxy analogues. These were shown to have some DNA alkylating properties though at concentrations $10^4$ times higher than that of the 6-hydroxy compounds.

The present invention relates to precursors of analogues CC-1065, which do not have the hydroxyl group in the B ring of the alkylating sub unit, and which are hence substantially inactive as DNA alkylating agents themselves.

It has been reported (Murray, G. I. et al., 15 Jul. 1997, Cancer Research, 57 m 3026–3031 and WO-A-9712246) that the enzyme CYP1B1, a member of the cytochrome P450 (CYP) family of xenobiotic metabolising enzymes, is expressed at a high frequency in a range of human cancers, including cancers of the breast, colon, lung, oesophagus, skin, lymph node, brain and testes, and that it is not detectable in normal tissues. This led to the conclusion that the expression of cytochrome P450 isoforms in tumour cells provides a molecular target for the development of new antitumour drugs that could be selectively activated by the CYP enzymes in tumour cells, although no drug examples were given. A number of other CYP isoforms have been shown to be expressed in various tumours. Many of the CYP's expressed in tumours are mentioned in Patterson, L H et al, (1999) Anticancer Drug Des. 14(6), 473–486.

In WO-A-99/40056 prodrugs of styrene- and chalcone-derivatives are described. The respective hydroxylated forms of the prodrugs, formed in situ, are potent tyrosine kinase (TK) inhibitors. Inhibition of TK activity contributes to tumour inhibition and cell destruction. The prodrugs were shown to be activated by microsomal preparations expressing CYP1B1 enzyme, and to have cytotoxic activity against cell lines expressing the same enzyme, whilst having much lower cytotoxic activity against cell lines not expressing the enzyme.

The present invention is directed to a new class of prodrugs which are expected to be hydroxylated in situ by CYP enzymes, in particular enzymes expressed at high levels in tumours. In particular the prodrugs are believed to be metabolisable by CYP1B1 enzyme. Some of the compounds are new. The present invention relates to the first therapeutic use of a broad range of compounds, and their synthesis as well as intermediates used therein.

There is provided according to the first aspect of the invention the new use of a compound of the general formula I or IA or a salt thereof in the manufacture of a composition for use in a method of treatment by therapy of an animal:

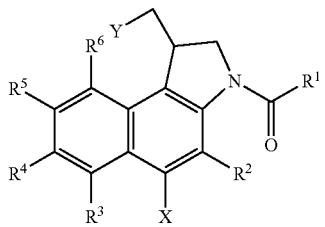

I

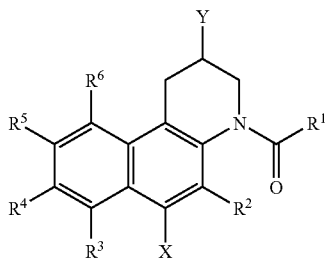

IA in which, X is H;
Y is a leaving group
$R^1$ is —Ar, $NH_2$, $OR^7$ or $R^7$;
$R^2$, $R^3$, $R^4$, $R^5$ and $R^6$ are each independently selected from H, $C_{1-4}$ alkyl, —OH, $C_{1-4}$ alkoxy, —CN, Cl, Br, I, —$NO_2$, —$NH_2$, —$NHR^{16}$, —$NR^{16}_2$, —$N^+R^{16}_3$, —NHCOR$^8$, —COOH, CONHR$^9$, —NHCOOR$^9$ and —COOR$^9$;
$R^7$, $R^8$ and $R^9$ are independently selected from $C_{1-4}$alkyl, optionally substituted phenyl, $C_{7-12}$-aralkyl, optionally substituted heteroaryl and a ligand;
Ar is selected from

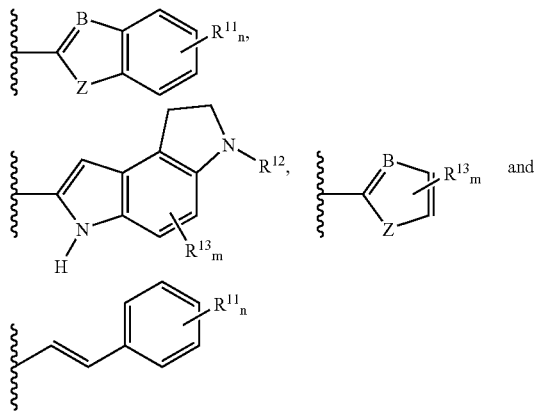

in which B is N or $CR^{10}$;
$R^{10}$ is selected from OH, $C_{1-4}$ alkoxy, $C_{1-4}$ alkyl, —$NO_2$, —$NH_2$, —CN, Cl, Br, I, —NHCOR$^{14}$, —COOH, —CONHR$^{15}$, —NHCOOR$^{15}$ and —COOR$^{15}$ and H;

Z is O, S, —CH═CH— or NH;
the or each $R^{11}$ is selected from OH, $C_{1-4}$ alkoxy, $C_{1-4}$ alkyl, —$NO_2$, —$NH_2$, —$NHR^{16}$, —$NR^{16}_2$, —$N^+R^{16}_3$, —CN, Cl, Br, I, —NHCOR$^{14}$, —COOH, —CONHR$^{15}$, —NHCOOR$^{15}$ and —COOR$^{15}$;
n is an integer in the range 0 to 4;
$R^{12}$ is H, —COAr$^1$, —CONH$_2$, —COOH, —COOR$^{15}$ or —COR$^{15}$;
the or each $R^{13}$ is selected from OH, $C_{1-4}$ alkoxy, $C_{1-4}$ alkyl, —$NO_2$, —$NH_2$, —$NHR^{16}$, —$NR^{16}_2$, —$N^+R^{16}_3$, —CN, Cl, Br, I, —NHCOR$^{14}$, —COOH, —CONHR$^{15}$, —NHCOOR$^{15}$ and —COOR$^{15}$;
m is 0, 1 or 2;
$R^{14}$ is selected from $C_{1-4}$ alkyl, optionally substituted phenyl, optionally substituted heteroaryl, $C_{7-12}$ aralkyl, Ar$^1$ and ligands;
$R^{15}$ is selected from $C_{1-4}$ alkyl, optionally substituted phenyl, $C_{7-12}$-aralkyl optionally substituted heteroaryl and ligands;
the or each $R^{16}$ is independently selected from $C_{1-4}$ alkyl, optionally substituted phenyl, $C_{7-12}$-aralkyl and optionally substituted heteroaryl; and
Ar$^1$ is selected from the same groups as Ar;
provided that no more than one group $R^{11}$ or $R^{13}$ in any one ring includes a group Ar$^1$.

Ar$^1$ is preferably

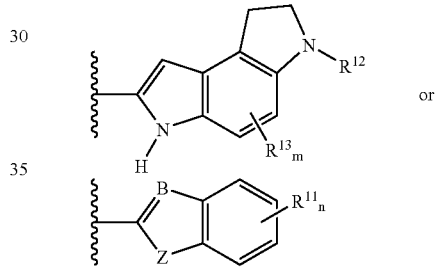

or

The animal which is treated is generally a human, although the compounds may also have veternary use. The indication treated is generally cancer including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

The tumour may, for instance, be defined as a tumour expressing high levels of CYP1B1.

In the invention, the leaving group Y is, for instance, in a group which has utility in nucleophilic substitution reactions. Suitable examples of leaving groups are —OCOOR$^{17}$, —OCONHR$^{18}$, Cl, Br, I, or —OSOOR$^{19}$, in which $R^{17}$, $R^{18}$ and $R^{19}$ are selected from $C_{1-4}$ alkyl, optionally substituted phenyl, $C_{7-12}$-aralkyl and optionally substituted heteroaryl. Most preferably the leaving group is a halogen atom, preferably chlorine.

Optional substituents in phenyl, aralkyl and heteroaryl groups are, for instance, $C_{1-4}$-alkyl, halogen, hydroxyl, $C_{1-4}$-alkoxy, —$NH_2$, —$NHR^{16}$, —$NR^{16}_2$, —$N^+R^{16}_3$, —$NO_2$, —CN, —COOH, —NHCOR$^{14}$, —CONHR$^{15}$, —NHCOOR$^{15}$, —COOR$^{15}$ etc.

In the present invention the term ligand includes a group having specific targeting characteristics, useful for instance in antibody or gene-directed enzyme prodrug-type environments. A ligand may be an oligopeptide, biotin, avidin or streptavidin, a polymeric group, an oligonucleotide or a protein. Preferably it has specific binding characteristics such as an antibody or fragment, an antigen, a sense or anti-sense oligo-nucleotide, or one of avidin, streptavidin and biotin, that is it is one component of a specific binding pair. Alternatively it may be a group designed for passive targeting, such as a polymeric group, or a group designed to prolong the stability or reduce immunogenicity such as a hydrophilic group. U.S. Pat. No. 5,843,937 discloses suitable ligands for conjugating to these types of actives and methods for carrying out the conjugation.

In a pharmaceutically active compound $R^1$ is other than $OR^7$.

In general, for optimised DNA binding ability, the group $R^1$ in a compound of the general formula I is a group Ar. Often the compound may include two aromatic groups joined to one another. In such compounds, one of the groups $R^{11}$ of the Ar group, or the group $R^{12}$, as the case may be, is a group $Ar^1$. Whilst for some compounds it may be desirable for three or more such aromatic groups to be linked, it is preferred that there is one group Ar and one group $Ar^1$. Thus in a group $Ar^1$ which is a pyrrolo-dihydroindole type of group, the group $R^{12}$ should be other than a group —$COAr^1$. In a group $Ar^1$ which is one of the other types of group there should preferably either be no substituents $R^{11}$ or $R^{13}$, as the case may be, or, if there are any substituents, no such substituents should include a group $Ar^1$.

According to one embodiment of the invention, the substituent Ar is a group

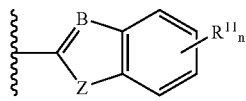

In such groups Ar, B is preferably $CR^{10}$. $R^{10}$ is preferably H. The definition of Z is preferably NH, although furan (Z=O) and thiophene (Z=S) analogues had been generated for conjugation to DNA alkylating units and may have useful DNA binding characteristics. Similarly, in a group $Ar^1$, the groups B and Z are selected amongst the same preferable groups. Preferably n is at least 1 and one of the groups $R^{11}$ is —$NHCOAr^1$. In this embodiment $Ar^1$ is preferably a group

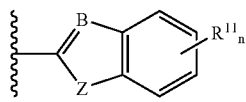

in which B and Z are the same as in Ar.

In another embodiment the substituent Ar is a group

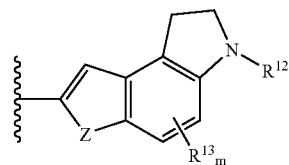

Preferably $R^{12}$ in Ar is other than —$COOR^{15}$, more preferably it is a group —$COAr^1$ in which $Ar^1$ preferably is the same type of group.

In both groups Ar and $Ar^1$, m in the indole type group is preferably zero.

In Ar and $Ar^1$, there may be several substituents $R^{11}$. Most preferably such substituents are selected amongst $C_{1-4}$-alkoxy groups.

In compounds of the formula I, the core indole ring of the DNA alkylating sub-unit is preferably unsubstituted in the benzene ring ($R^2$ is hydrogen), whilst the benz ring may be unsubstituted ($R^3$, $R^4$, $R^5$ and $R^6$ are all hydrogen), or one or more of $R^3$ to $R^6$ represents a cyano group, an alkoxy group, a group —$COOR^{10}$, or a $C_{1-4}$-alkyl group (preferably methyl).

In one preferred embodiment $R^5$ is a alkoxy, preferably methoxy and $R^2$, $R^3$, $R^4$, $R^6$ are all H.

In another embodiment $R^5$ is cyano and $R^2$, $R^3$, $R^4$ and $R^6$ are H.

In the compounds of the formula I, X is H. It is believed that, hydroxylation of the compound will occur in situ at the carbon atom to which X is attached, thereby activating the compound enabling it to act as a DNA alkylating agent.

Many of the compounds of the general formula I and salts thereof are believed to be novel compounds. According to a further aspect of the invention there is provided a new compound of the general formula II or a salt thereof

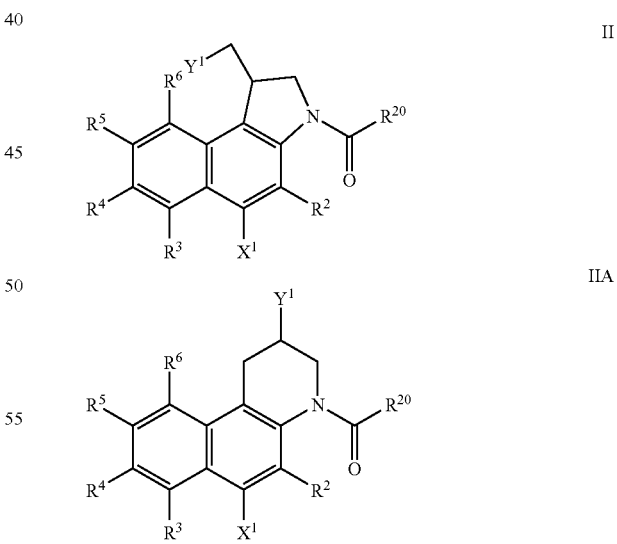

in which $R^2$, $R^3$, $R^5$ and $R^6$ are as defined above
$X^1$ is H;
$Y^1$ is a leaving group;
$R^{20}$ is —$R^7$, —$OR^7$, —$NH_2$ or $Ar^2$;
$R^7$ is as defined above;
$Ar^2$ is selected from

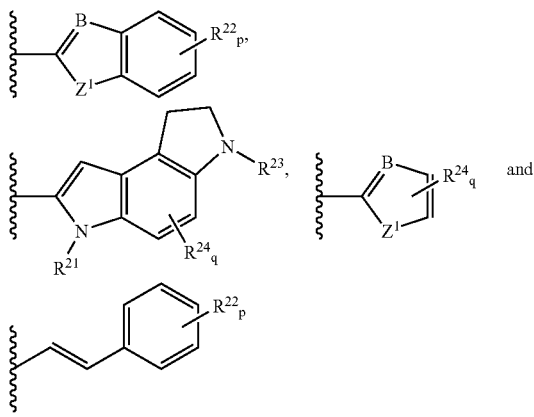

in which $B^1$ is N or $CR^{22}$;

$Z^1$ is O, S, —CH=CH— or $NR^{21}$;

$R^{21}$ is an amine protecting group;

the or each $R^{22}$ is selected from OH, $C_{1-4}$ alkoxy $C_{1-4}$ alkyl, $NO_2$, —$NHR^{21}$, —$NHR^{26}$, —$NR^{26}_2$, —$N^+R^{26}_3$, —CN, Cl, Br, I, —$NHCOR^{25}$, —COOH, —$CONHR^7$ and —$COOR^{25}$;

p is an integer in the range 0 to 4;

$R^{23}$ is H, $COAr^3$, —$CONH_2$, —COOH, —$CONHR^7$ or —$COR^7$ or is an amine protecting group;

the or each $R^{24}$ is selected from OH, $C_{1-4}$ alkoxy $C_{1-4}$ alkyl, $NO_2$, —$NHR^{21}$, —$NHR^{26}$, —$NR^{26}_2$, —$N^+R^{26}_3$, —CN, Cl, Br, I, —$NHCOR^{25}$, —COOH, —$CONHR^7$ and —$COOR^7$;

q is 0, 1 or 2;

$R^{25}$ is selected from $C_{1-4}$ alkyl; optionally substituted phenyl, optionally substituted heteroalkyl, $C_{7-12}$ aralkyl $Ar^3$ and a ligand.

$R^{26}$ is selected from $C_{1-4}$ alkyl, optionally substituted phenyl, $C_{7-12}$-aralkyl and optionally substituted heteroaryl; and $Ar^3$ is selected from the same groups as $Ar^2$ provided that no more than one $R^{22}$ or $R^{24}$ in any one ring includes a group $Ar^3$.

$Ar^3$ is preferably

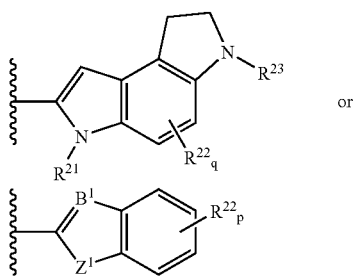

or

Compounds of the formula II or IIA, in which primary or secondary amine nitrogen atoms are protected are generally deprotected before being used in pharmaceutical compositions. Examples of amine protecting groups $R^{21}$ or $R^{23}$ are benzyl, benzyloxycarbonyl, tertiary butyloxycarbonyl (BOC), fluorenyl-N-methoxy-carbonyl (FMOC) and 2-[biphenylyl-(4)]-propyl-2-oxycarbonyl. Where more than one amine group is protected in the molecule, the protecting groups may be the same or different. In a particularly useful series of compounds of the general formula II and II A, $R^{20}$ is $OR^7$ and $R^7$ is an amine protecting group different to $R^1CO$. In another preferred series $R^{20}$ is other than $OR^7$.

In compounds of the general formula II and IIA, $R^{20}$ is preferably $Ar^2$, and/or $Y^1$ is preferably selected from —$OCOOR^{17}$, —$OCONHR^{18}$, Cl, Br, I, or —$OSOOR^{19}$, in which $R^{17}$, $R^{18}$ and $R^{19}$ are selected from $C_{1-4}$alkyl, optionally substituted phenyl, $C_{7-12}$-aralkyl and optionally substituted heteroaryl. Most preferably the leaving group is a halogen atom, preferably chlorine.

The present invention further provides pharmaceutical compositions comprising compounds of the formula I or IA and a pharmaceutically acceptable excipient. Pharmaceutical compositions may be suitable for intramuscular, intraperitoneal, intrapulmonary, oral or, most preferably, intravenous administration. The compositions contain suitable matrixes, for example for controlled or delayed release. The compositions may be in the form of solutions, solids, for instance powders, tablets or implants, and may comprise the compound of the formula I in solid or dissolved form. The compound may be incorporated in a particulate drug delivery system, for instance in a liquid formulation. Specific examples of suitable excipients include lactose, sucrose, mannitol, and sorbitol; starch from corn, wheat, rice, potato, or other plants; cellulose, such as methyl cellulose, hydroxypropylmethylcellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate. Solid compositions may take the form of powders and gels but are more conveniently of a formed type, for example as tablets, cachets or capsules (including spansules). Alternative, more specialised types of formulation including liposomes, nanosomes and nanoparticles.

Compounds of the formula I may be synthesised using techniques analogous to those summarised by Boger et al 1997, op. cit. It is convenient to form the DNA alkylating sub unit in one series of steps and to attach this through the nitrogen atom of the dihydro-pyrrole or tetrahydroquinoline (C) ring to the rest of the molecule. The DNA alkylating sub-unit may be conjugated to DNA binding sub-units synthesised as described in Boger et al, 1997 op. cit., for instance the PDE-I and PDE-II sub-units described in that reference. The DNA binding subunits are those including the groups Ar and $Ar^1$.

According to a further aspect of the invention there is provided a new synthetic method in which a compound of the formula III or IIIA

III

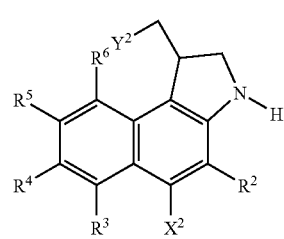

-continued

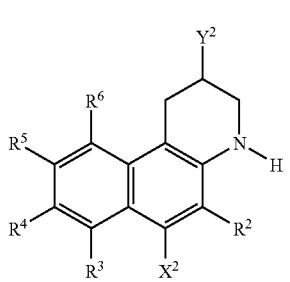

IIIA in which $R^2$, $R^3$, $R^4$, $R^5$ and $R^6$ are as defined above;

$X^2$ is H; and $Y^2$ is a leaving group or a hydroxyl or protected hydroxyl group; is reacted with a compound of the general formula IV $$R^{27}COY^3 \qquad \text{IV}$$

in which $R^{27}$ is selected from $C_{1-4}$-alkyl, optionally substituted phenyl, $C_{7-12}$-aralkyl, optionally substituted heteroaryl and $Ar^4$;

$Ar^4$ is selected from

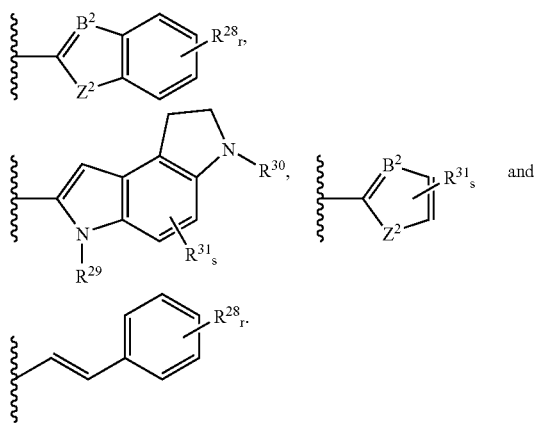

in which $B^2$ is N or $CR^{32}$;

$Z^2$ is O, S, —CH=CH— or $NR^{33}$;

the or each $R^{28}$ is selected from $C_{1-4}$-alkoxy, $C_{1-4}$-alkyl, $NO_2$, CN, Cl, Br, I, —$NHR^{33}$, —$NHR^{35}$, —$NR^{35}{}_2$, —$N^+R^{35}{}_3$—, —$NHCOR^{34}$, —COOH, —$CONHR^{36}$ and —$COOR^{36}$;

r is an integer in the range 0 to 4;

$R^{29}$ is an amine protecting group;

$R^{30}$ is an amine protecting group, —$CONH_2$, —COOH, —$COR^{36}$ or —$COAr^5$;

the or each $R^{31}$ is selected from $C_{1-4}$-alkoxy, $C_{1-4}$-alkyl, $NO_2$, CN, Cl, Br, I, —$NHR^{33}$, —$NHR^{35}$, —$NR^{35}{}_2$, —$N^+R^{35}{}_3$—, —$NHCOR^{34}$, —COOH, —$CONHR^{36}$ and —$COOR^{36}$;

s is 0, 1 or 2;

$R^{32}$ is selected from H, $C_{1-4}$-alkoxy, $C_{1-4}$-alkyl, $NO_2$, CN, Cl, Br, I, —$NHR^{53}$, —$NHR^{35}$, —$NHR^{35}{}_2$, —$N^+R^{35}{}_3$, $NHCOR^{34}$, COOH, —$CONHR^{36}$ and $COOR^{36}$;

$R^{33}$ is an amine protecting group;

$R^{34}$ is selected from $Ar^5$, $C_{1-4}$-alkyl, optionally substituted phenyl, $C_{7-12}$-aralkyl, optionally substituted heteroaryl and a ligand;

$R^{35}$ is selected from $C_{1-4}$-alkyl, optionally substituted phenyl, $C_{7-12}$-aralkyl and optionally substituted heteroaryl;

$R^{36}$ is selected from $C_{1-4}$-alkyl, optionally substituted phenyl, $C_{7-12}$-aralkyl optionally substituted heteroaryl and a ligand;

$Ar^5$ is selected from the same groups as $Ar^4$ and $Y^3$ is a leaving group provided that no more than one $R^{28}$ or $R^{31}$ in any one ring includes a group $Ar^5$.

$A^5$ is preferably

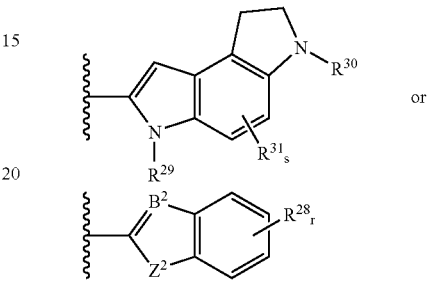

$Y^3$ is, for instance, selected amongst the preferred leaving groups listed above for Y. Most suitably the definition of $Y^3$ is Cl. Alternatively, the group $Y^3$ may be OH. In this case, it may be necessary to include a coupling agent to assist in the coupling reaction.

The reaction between the compound of the general formula III or IIIA and the carboxylic acid or derivative of the general formula IV is carried out under conditions allowing such coupling to take place. Such conditions are is similar to those generally used for formation of peptide bonds, for instance as used in peptide synthetic methods.

$Y^2$ is a hydroxy or protected hydroxyl group or a leaving group, which may be the same as Y, or may be converted to Y in a subsequent step.

After the coupling process, it may be desirable to deprotect one or more of the protected amine groups. If further reaction, for instance with other derivatising agents such as glycosyl compounds, peptides, polymers etc is desired through any such amine groups, it may be desirable to deprotect only those to which subsequent reaction to to take place, whilst retaining the other amine groups in a protected form. Selection of suitable amine protecting groups and protection and deprotection protocols may be made using techniques commonly utilised in peptide chemistry.

It is believed that some of the intermediates of the general formula III or IIIA may be novel compounds. A novel compound may have the general formula V or VA

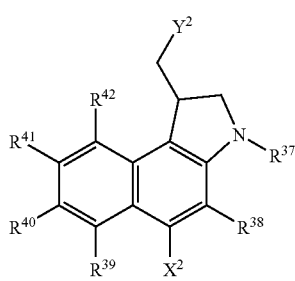

V

-continued

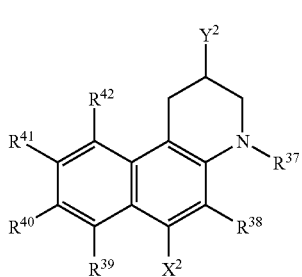

VA

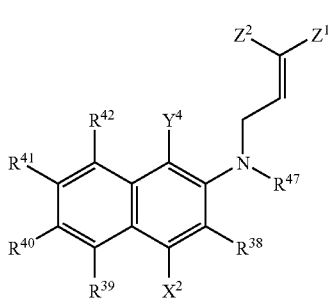

VI in which $R^{38}$, $R^{39}$, $R^{40}$, $R^{41}$ and $R^{42}$ are selected from H, $C_{1-4}$-alkyl, —OH, $C_{1-4}$-alkoxy, —CN, Cl, Br, I, $NO_2$, $NHR^{43}$, —$NHCOR^{44}$, —$NR^{45}{}_2$, —$N^+R^{45}{}_3$, —COOH, —$CONHR^{46}$ and —$COOR^{46}$ $X^2$ is H;

$Y^2$ is a leaving group or a hydroxyl or protected hydroxyl group;

$R^{37}$ is H or an amine protecting group;

$R^{43}$ is selected from H, $C_{1-4}$alkyl, optionally substituted phenyl, $C_{7-12}$-aralkyl, and optionally substituted heteroaryl an amine protecting group;

$R^{44}$ is selected from $C_{1-4}$alkyl, optionally substituted phenyl, $C_{7-12}$-aralkyl, optionally substituted heteroaryl and a ligand;

each $R^{45}$ is selected from $C_{1-4}$alkyl, optionally substituted phenyl, $C_{7-12}$-aralkyl and optionally substituted heteroaryl; and $R^{46}$ is selected from $C_{1-4}$alkyl, optionally substituted phenyl, $C_{7-12}$-aralkyl, optionally substituted heteroaryl and a ligand.

In compounds of the general formula II, in the compound ready for reaction with a carboxylic acid derivative, for instance of the general formula IV, $R^{24}$ is H. Precursors for such compounds have the ring nitrogen atom in protected form, that is in which $R^{37}$ represents a protecting group.

In compounds of the formula V, the group $Y^2$ may be selected amongst those defined above for leaving group Y. The nature of the group $Y^2$ should be selected having regard to the nature of the reagent with which the compound of the formula III/V is to react in a subsequent step, for instance with a compound of the general formula IV, such that the group $Y^2$ is not deactivated and does not form a dimer of compounds of the formula III or V. Suitable examples of leaving group $Y^2$ are Cl and Br.

The compound of the formula III or IIIA and V or VA may be prepared in a preliminary step including a cyclisation step in the presence of a catalyst using as the starting material an aniline compound having a leaving group substituent $Y^4$ at the carbon atom ortho to the amine group substituent, and an N-substituent which is a group —$CH_2CH$=$CHY^5$, in which the aniline derivative is reacted under cyclisation conditions, to form a dihydropyrrole or a di- or tetra hydroquinoline ring. The starting compound for such a reaction may be represented by the general formula VI in which $R^{38}$ through $R^{42}$ and $X^2$ are the same as in the compound of the formula IV;

$R^{47}$ is an amine protecting group, one of $Z^1$ and $Z^2$ is $Y^5$ and the other is H;

$Y^5$ is a leaving group which is different from or the same as $Y^2$; and $Y^4$ is the radical leaving group.

For cyclisation to form a dihydropyrrole ring, the group $Z^1$ is $Y^5$ and $Y^5$ is either H or a leaving group, preferably the same group as $Y^2$ wherein the group $Y^5$ is not effective as a leaving group in this step of the synthesis. The reaction is conducted in the presence of a suitable catalyst, optionally in the presence of a free radical trap. The group $Y^4$ should be a radical leaving group, such as halogen, preferably Br or I. Suitable radicals for carrying out the cyclisation reaction using a compound VI in which $Y^5$ is H are nitroxy compounds such as 2,2,6,6-tetramethylpiperidinyloxy (TEMPO). Where Y, is a leaving group the cyclisation may be carried out in the presence of a radical derived from azoisobutyronitrile (AIBN). Suitable catalysts for such a radical cyclisation step are tin hydride compounds such as tributyl tin hydride. Such a synthetic route is illustrated in Examples 1 and 3.

For cyclisation to form a 6-membered ring it is preferred to use a compound VI in which $Z^2$ is $Y^5$ and $Y^5$ is a leaving group, preferably a trialkyl stannyl group, and to carry out the reaction in the presence of a suitable catalyst palladium complexes such as tetrakis (triphenylphosphine) palladium (0), bis(triphenyl phosphine) palladium (II) chloride or palladium (II) acetate. The dihydroquinoline intermediate is oxidised to form a further is intermediate which is an epoxide, for instance using a peroxide reagent. The epoxide intermediate is reduced using a suitable selective reducing agent such as a dialkyl aluminium hydride to produce the corresponding tetrahydroquinoline alcohol which is subsequently halogenated, for instance using carbon tetrachloride/triphenyl phosphine. This reaction is illustrated in Example 2.

The compound of the general formula VI may be produced by alkylation of the sodium salt of the corresponding aniline derivative with a 1,3-dihalo propene compound.

The carboxylic acid derivative of the general formula V may be synthesised using the methods generally described in Boger et al, 1997 op.cit. for instance PDE-I and PDE-II may be synthesised using the Umezawa synthesis, the Rees-Moody synthesis, the Magnus synthesis, the Cava-Rawal synthesis, the Boger-Coleman synthesis, the Sundberg synthesis, the Martin synthesis, the Tojo synthesis. Indole-2-carboxylic acid is commercially available. Other analogues of the DNA binding sub-units of the duocarmycins, and reactive carboxylic acid derivatives thereof are described by Boger et al, op.cit and in U.S. Pat. No. 5,843,937.

The present invention relates to the creation of a range of prodrugs that have little or no cytotoxic effects when in their normal state, but are highly cytotoxic (i.e. have a substantially increased cytotoxicity) when activated by oxidation or hydroxylation by CYP enzymes. This provides for a self-targeting drug delivery system in which a non cytotoxic (or negligibly cytotoxic) compound can be administered to a patient, for example in a systemic manner, the compound then being activated at the site of the tumour cells (intratumoural activation) to form a highly cytotoxic compound which acts to kill the tumour cells. The fact that the CYP isoforms are not expressed by normal cells mean that the activation of the compound only occurs at the site of the tumour cells and therefore only tumour cells are affected, thus providing a self-targeting system.

The prodrugs of the present invention have the distinct advantage of being useful in the treatment of tumours at any site in the body, meaning that even tumours that have undergone metastasis (which are normally not susceptible to site specific therapies) may be treated.

The prodrug may be an antitumour prodrug. Examples of tumours include cancers (malignant neoplasms) as well as other neoplasms e.g. innocent tumours. The prodrug may be activated by hydroxylation by isoforms of cytochrome P450's.

In a variation of the normal procedure which relies upon CYP expression within tumour cells to effect selective hydroxylation and hence activation of the prodrugs, the selectivity between tumour tissue and normal tissue can be enhanced in a two part procedure. Thus (a) infecting tumor cells with a viral vector carrying a cytochrome P450 gene and a cytochrome P450 reductase gene, wherein expression of cytochrome P450 gene and cytochrome P450 reductase gene by tumor cells enables the enzymatic conversion of a chemotherapeutic agent to its cytotoxic form within the tumor, whereby the tumor cells become selectively sensitized to the prodrug chemotherapeutic agent (b) contacting tumor cells with the prodrug chemotherapeutic agent whereby tumor cells are selectively killed.

These prodrugs are benz(e)dihydroindole or benz-tetrahydroquinoline derivatives. Their specific use as antitumour prodrugs has not been previously suggested or disclosed, nor has the suggestion that they are prodrugs having an activated hydroxylated form. Where compounds of formula (I) have been previously identified and made, they have not been identified as anti-tumour agents due to their poor (or negligible) cytotoxicity. Thus the intratumoural hydroxylation of the prodrugs of the present invention provides them with a surprising and unexpected efficacy.

Hydroxylated forms of the prodrugs are potent DNA alkylating agents that bind in the minor groove of DNA and alkylate the purine bases at the N3 position. As such, they are potent cytotoxic agents whose exact biological mechanism of action is unknown but involves the disruption of template and other functions of DNA. General inhibition of template function of DNA will affect and be generally cytotoxic to all dividing cells in the body and lead to unacceptable side effects in a therapeutic setting. However, the targetted production of hydroxylated forms only in tumour cells that overexpress particular isoforms of cytochrome P450's will lead to a specific cytotoxic effect only in those cells. The non-hydroxylated forms are essentially non-toxic to all cells.

The following examples illustrate the invention.

EXAMPLE 1

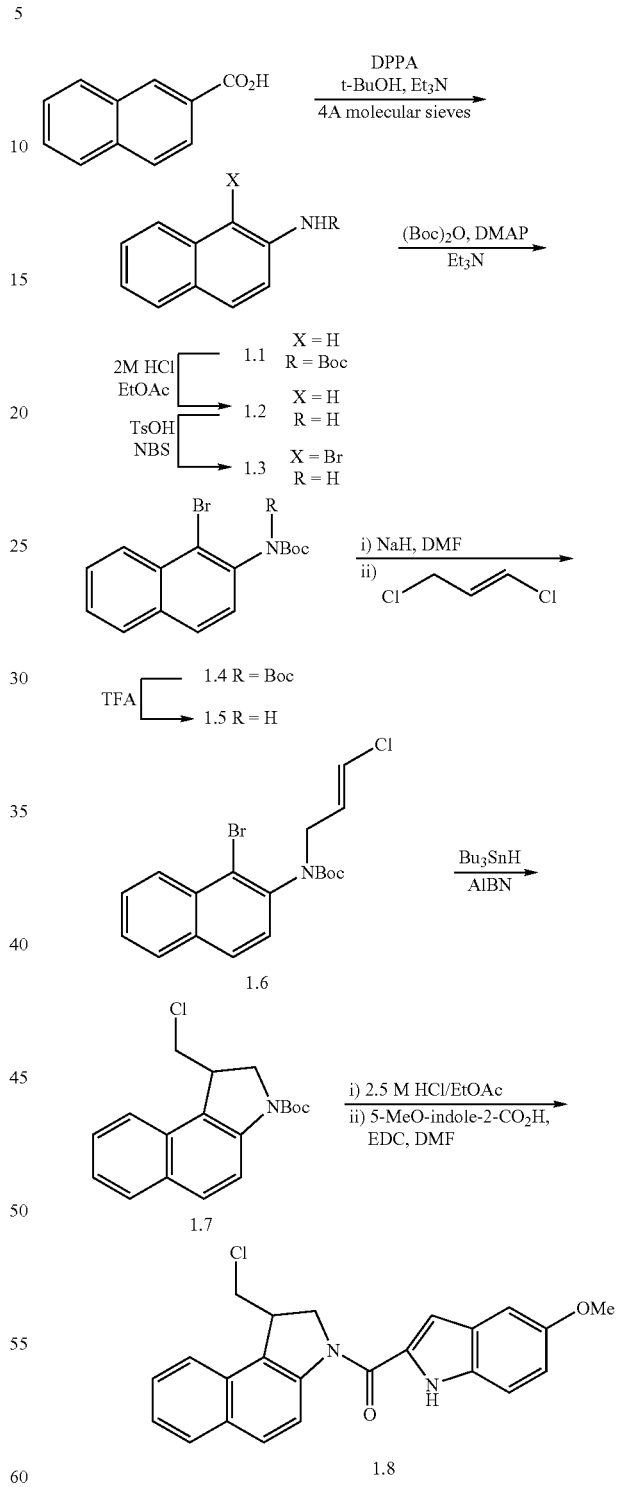

1.1 N-(tert-Butyloxycarbonyl)napthylamine

A solution of 2-napthoic acid (100 mg, 0.581 mmol) in t-BuOH (33 mL) was treated with $Et_3N$ (96 μL, 0.7 mmol) and 4 Å molecular sieves (1 g). Diphenyl phosphorylazide (0.15 ml, 0.7 mmol) was added, and the reaction mixture was warmed to reflux for 14 h. The mixture was cooled to 25° C. and the solvent removed under vacuum. The residue was dissolved in EtOAc (10 mL) and the organic phase was washed with 10% aqueous HCl (3×15 mL), dried (MgSO$_4$) and concentrated. Purification by flash chromatography (SiO$_2$, 10% EtOAc in hexanes) afforded 2 (0.108 mg, 77%) as a pale yellow solid. FABMS (NBA/NaI) 243([M+H]$^+$ expected 243) 269 ([M+Na]$^+$ expected 269).

1.2 2-Napthylamine

Compound 1.1 (1.5 g, 6.17 mmol) was dissolved in EtOAc (10 mL) to which was added 2.5 M HCl in EtOAc. The reaction mixture was stirred for 30 min. The resulting solution was then diluted with sat'd aq. NaHCO$_3$ (50 mL) and extracted with EtOAc (2×25 mL). The combined organic layers were dried (MgSO$_4$) and concentrated. The residue was crystalised from 20% EtOAc in hexane to afford 3.3 (0.74 g, 84%) as pale brown crystals: $^1$H NMR (250 MHz, CDCl$_3$) δ ppm 7.12–7.32 (m, 3H), 6.96 (t, 1H), 6.80 (t, 1H), 6.56 (s, 1H), 6.52 (dd, 1H), 3.46 (br s, 2H); FAB MS (NBA/NaI) 143 ([M+H]$^+$ expected 143), 165 ([M+Na]$^+$ expected 165).

1.3 1-Bromo-2-napthylamine

A solution of 1.2 (100 mg, 0.7 mmol), TsOH (48 mg, 0.28 mmol) in THF (6 mL) was stirred and cooled to 0° C. To the resulting mixture NIS (125 mg, 0.56 mmol) and THF (6 mL) were added and the solution was allowed to warm to 25° C. After 3 h, additional NIS (31 mg, 0.14 mmol) was added. After 1 h, the mixture was diluted with 10% aqueous NaHCO$_3$ (10 mL) and extracted with CHCl$_3$ (3×10 mL). The organic layers were combined, dried (MgSO$_4$) and concentrated. The residue was purified by flash chromatography (SiO$_2$, 30% EtOAc in hexane) to afford 1.3 (110 mg, 59%) as a brown-yellow oil $^1$H NMR (250 MHz, CDCl$_3$) δ ppm 8.04 (d, 1H), 7.68 (d, 1H), 7.62 (d, 1H), 7.50 (t, 1H), 7.28 (t, 1H), 7.00 (d, 1H), 4.40 (br s, 2H); FABMS (NBA/NaI): 221 ([M+H]$^+$ expected 221), 243 ([M+Na]$^+$ expected 243).

1.4 N-Di(tert-butyloxycarbonyl)-1-bromo-2-napthylamine

A solution of 1.3 (100 mg, 0.37 mmol) in CH$_2$Cl$_2$ (5 mL) was treated with Boc-dicarbonate (219 mg, 1.0 mmol), Et$_3$N (62 µl, 0.45 mmol) and DMAP (4.5 mg, 0.037 mmol). The reaction was refluxed at 50° C. for 24 h. The resulting mixture was washed with H$_2$O (2×10 mL), 5% HCl (10 mL) and finally again with H$_2$O (10 mL). The organic layers were combined, dried (MgSO$_4$) and concentrated. The reaction was purified by flash chromatography (SiO$_2$ CH$_2$Cl$_2$/hexane 1:1) to afford 1.4 (125 mg, 72%) as a colourless solid. $^1$H NMR (250 MHz, CDCl$_3$) δ ppm 8.32 (d, 1H), 7.86 (d, 1H), 7.80 (d, 1H), 7.52–7.68 (m, 2H), 7.32 (d, 1H), 1.50 (s, 18H); FABMS (NBA/NaI) 422 ([M+H]$^+$ expected 422), 446 ([M+Na]$^+$ expected 446).

1.5 N-(tert-Butyloxycarbonyl)-1-bromo-2-napthylamine

Compound 1.4 (50 mg, 0.107 mmol) was treated with a solution of TFA (16 µL, 0.213 mmol) in CH$_2$Cl$_2$ (2 mL) and stirred for 45 min. The mixture was concentrated and recrystallised from hexane to afford 1.5 (13 mg, 34%) as white crystals. FABMS (NBA/NaI) 323 ([M+H]$^+$ expected 323), 346 ([M+Na]$^+$ expected 346).

1.6 N-(tert-Butyloxycarbonyl)-N-(3-chloro-2-propen-1-yl)-1-bromo-2-napthylamine

A solution of 1.5 (50 mg, 0.14 mmol) and DMF (5 mL) was cooled to 0° C. and NaH (9.8 mg, 0.408 mmol) was added. The resulting mixture was stirred for 15 min and 1,3 dichloropropene (38 µL, 0.41 mmol) was added. The is solution was allowed to warm to 25° C. and stirred for 90 min. The mixture was concentrated and the residue was purified by flash chromatography (SiO$_2$, 10% EtOAc in hexane) to afford 1.6 (56 mg, 93%) as a clear film. FABMS (NBA/NaI) 396 ([M+H]$^+$ expected 396), 418 ([M+Na]$^+$ expected 418).

1.7 3-(tert-Butyloxycarbonyl)-1-(chloromethyl)-1,2-dihydro-3H-benz[e]indole

A solution of 1.6 (55 mg, 0.12 mmol) and AIBN (8 mg, 0.05 mmol) in anhydrous toluene (5 mL) was degassed for 15 min with N$_2$ and then heated to 90° C. Bu$_3$SnH (65 µl, 0.25 mmol) was added in four portions over 1 h and the resulting mixture was stirred for 1 h. The soluion was then concentrated and purified by flash chromatography (SiO$_2$, 10% EtOAc in hexane) to afford impure 3.8. The solid was then dissolved in EtOAc (2 mL) to which a 1M KF solution (1 ml) in EtOAc (1 ml) was added. The solution was stirred for 45 mins after which the insoluble precipitate was filtered and the remaining solution concentrated to afford pure 1.7 (34 mg, 87%) as a pale yellow oily film. FABMS (NBA/NaI) 317 ([M+H]$^+$ expected 317).

1.8 1-(Chloromethyl)-3-[(5-methoxyindol-2-yl)carbonyl]-1,2-dihydro-3H-benz[e]indole Compound 1.7 (10 mg, 0.03 mmol) was treated with 2.5 M HCl in EtOAc (100 µL) and the solution was stirred for 30 min. The solvent was removed under a stream of nitrogen and the grey residue was dissolved in DMF (1 mL). 5-Methoxyindole-2-carboxylic acid (17 mg, 0.09 mmol) and EDC (17 mg, 0.09 mmol) were added and the mixture stirred for 16 h. Solvent was removed in vacuo and the residue subjected to flash chromatography (SiO$_2$, EtOAc/hexanes 1:1) to give the product as a red oil (11 mg, 94%). FABMS (NBA/NaI) 391 (M+H$^+$ expected 391).

EXAMPLE 2

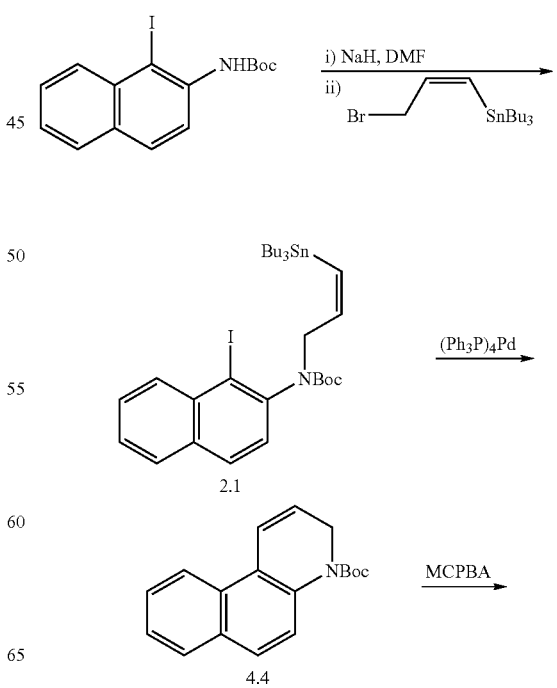

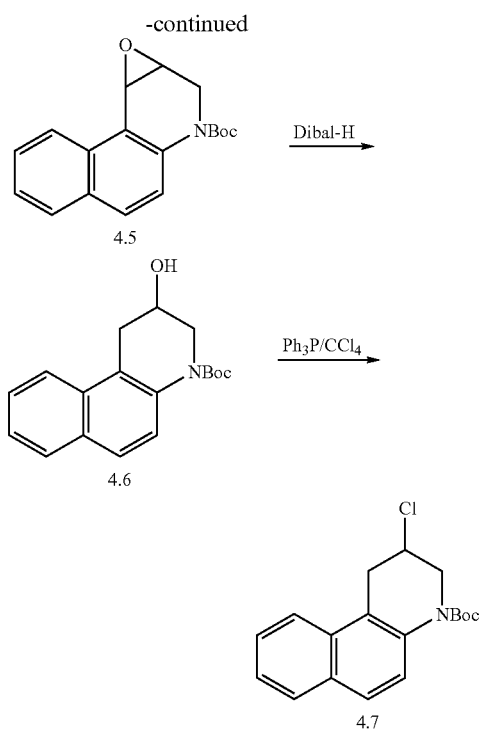

2.1  2-[N-(3-(tributylstannyl)-2-propen-1-yl)-N-((tert-butyloxy) carbonyl)]amino-1-napthalene 1-benzoyl-5-(tert-butyloxycarbonyl)amino-4-iodoindole (100 mg, 0.22 mmol) was stirred in DMF (1 mL) and sodium hydride (26 mg, 0.66 mmol, 60% dispersion in oil, 3 equiv.) was added. After 15 min, the suspension was treated with E/Z-1-tributylstannyl-3-bromopropene (270 mg, 0.66 mmol, 3 equiv) and the resulting solution was stirred at RT for 16 h. The solution was concentrated and water (10 mL) was added. The aqueous solution was extracted with ethyl acetate (3×10 mL), the organic layers combined, dried and concentrated. Flash chromatography (SiO$_2$, 10% ethyl acetate/hexanes) gave the product (120 mg, 78%) as a yellow solid. FABMS (NBA/NaI): 699 (M+H$^+$ expected 699).

2.2  1,2-dihydro-1-((tert-butyloxy)carbonyl)-5,6-benzoquinoline

1-Benzoyl-5-[N-(3-(tributylstannyl)-2-propen-1-yl)-N-((tert-butyloxy)carbonyl)]amino-4-iodoindole (100 mg, 0.14 mmol) and tetrakis(triphenylphosphine) palladium(0) (32 mg, 0.2 equiv) were stirred in toluene (2 mL) at 50° C. under N$_2$ for 4 h. The solvent was then removed in vacuo. Chromatography (SiO$_2$, 10% ethyl acetate/hexanes) gave the product as a red oil (38 mg, 99%). FABMS (NBA/NaI): 282 (M+H$^+$ expected 282).

2.3  3,4-epoxy-1-((tert-butyloxy)carbonyl)-1,2,3,4-tetrahydro-5,6-benzoquinoline 1,2-dihydro-1-((tert-butyloxy)carbonyl)-5,6-benzoquinoline (100 mg, 0.36 mmol) and MCPBA (91 mg, 0.54 mmol, 1.5 equiv) were stirred in CH$_2$Cl$_2$ (2 mL) at −30° C. under N$_2$ for 6 h. The solvent was removed in vacuo. Chromatography (SiO$_2$, 10% ethyl acetate/hexanes) gave the product (101 mg, 95%). FABMS (NBA/NaI): 298 (M+H$^+$ expected 298).

2.4  4-hydroxy-1-((tert-butyloxy)carbonyl)-1,2,3,4-tetrahydro-5,6-benzoquinoline 3,4-epoxy-1-((tert-butyloxy)carbonyl)-1,2,3,4-tetrahydro-5,6-benzoquinoline. (100 mg, 0.34 mmol) was treated with Dibal-H (91 mg, 0.54 mmol, 1.5 equiv) in THF (2 mL) at −78° C. to −30° C. under N$_2$. After 1 h, the reaction was quenched by the addition of water (2 mL) and the resulting solution was extracted with ethyl acetate (3×10 mL), the organic layers combined, dried and concentrated. The solvent was removed in vacuo. Chromatography (SiO$_2$, 10% ethyl acetate/hexanes) gave the product (55 mg, 54%) as a colourless solid. FABMS (NBA/NaI): 300 (M+H$^+$ expected 300), 322 (M+Na$^+$ expected 322).

2.5  4-Chloro-1-((tert-butyloxy)carbonyl)-1,2,3,4-tetrahydro-5,6-benzoquinoline 4-hydroxy-1-((tert-butyloxy)carbonyl)-1,2,3,4-tetrahydro-5,6-benzoquinoline (100 mg, 0.33 mmol) in CH$_2$Cl$_2$ (2 mL) was treated with a prepared solution of PPh$_3$ (175 mg, 0.66 mmol, 2 equiv) and CCl$_4$ (200 mL) in CH$_2$Cl$_2$ (2 mL) at RT. After 4 h, the solvent was removed in vacuo. Chromatography (Silica gel, 2×15 cm, 10% ethyl acetate/hexanes) gave the chloride as an oil (65 mg, 63%). FABMS (NBA/NaI): 318 (M+H$^+$ expected 318), 340 (M+Na$^+$ expected 340). The product may subsequently be deprotected and conjugated to a DNA-binding subunit such as 5-methoxyindole-2-carboxylic acid by process steps analogous to example 1.8.

EXAMPLE 3

Biological Testing of Compound 1.8
Materials and Methods 3.1 Incubation Mixtures of Test Compound And Microsomes Test compound activation by CYP enzymes was carried out using NADPH supplemented rat liver microsomes. Incubation mixtures comprised microsomal protein (1 mg/ml), reduced-nicotinamide adenine dinucleotide phosphate (NADPH, 10 mM) and phosphate buffer (pH7.4, 100 mM). Test compound (0.01–100 µM final concentration) in DMSO (20 µl) was added to the microsomal incubation mixtures (0.5 ml) and incubated for 60 min at 37 C. Control incubates contained test compound and microsomal incubation mixture terminated at 0 time. All incubations were terminated by addition of an equal volume of ice-cold acetonitrile and microfuged for 3 min. Aliquots of the supernatant were added to cells in culture and cytotoxicity determined as described below.

3.2 Cell Culture Based Cytotoxicity Measurement

Chinese Hamster Ovary (CHO) cell were grown in MEM supplemented with 10% dialysed FBS and G418 (400 µg/ml). All cells were seeded at an initial density of 1000 cells/well in 96-well-plates, incubation at 37° C. for 24 hours. Aliquots (0.1 ml) of the test compound/microsomal/acetonitrile supernatnant was then added to the CHO cells. Cells were then incubated for 24 hours at 37° C., 5% CO$_2$. After this time period MTT (50 µl; 2 mg/ml stock solution) was added to each well and cells were incubated for a further 4 hours. During this time period MTT, a hydrogen acceptor tetrazolium salt, is reduced to formazan dye by mitochondrial dehydrogenase of viable cells. The media was aspirated from cells and DMSO (100 µl/well) added to solubilise the coloured formazan dye. Absorbance of the formazan dye in the 96-well-plates was then determined at 550 nm. The effect of microsomal activation by the test compound on the arrest of CHO cell growth could be determined by comparing the IC$_{50}$ (concentration that inhibited cell growth by 50%) with and without microsomal incubation.

Results

| | CHO IC50 (μM) | | |
|---|---|---|---|
| compound | +activation | −activation | AF |
| 1.8 | 0.1 ± 1.2 | 1.5 ± 0.53 | 15.0* |

AF = activity factor i.e. the ratio of IC$_{50}$ cytotoxicity values obtained for + compound 1.8 activation
*represents significance at p > 0.05.

Effect of compound 3.9 and its metabolism (activation) product on the survival of Chinese hamster ovary cells in culture. Cells were incubated for 24 hours with supernatants from reaction mixtures of compound 3.9 with NADPH fortified rat liver microsomes. IC$_{50}$ represents the concentration of drug required to inhibit cell growth by 50%. Values are expressed as the mean+sd for three experiments. See methods for full details of metabolism.

The invention claimed is:

1. A pharmaceutical composition comprising a compound of the general formula I

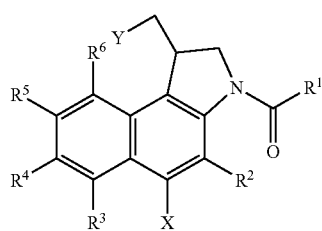

in which X is H;
Y is a leaving group;
R$^1$ is —Ar, NH$_2$, R$^7$ or —OR$^7$;
R$^2$, R$^3$, R$^4$, R$^5$ and R$^6$ are each independently selected from the group consisting of H, C$_{1-4}$ alkyl, —OH, C$_{1-4}$ alkoxy, —CN, Cl, Br, I, —NO$_2$, —NH$_2$, —NHR$^{16}$, —NR$^{16}$$_2$, —N$^+$R$^{16}$$_3$; —NHCOR$^8$, —COOH, —CONHR$^9$, —NHCOOR$^9$ and —COOR$^9$;
R$^7$, R$^8$ and R$^9$ are independently selected from the group consisting of C$_{1-4}$ alkyl, optionally substituted phenyl, C$_{7-12}$-aralkyl, optionally substituted heteroaryl and a ligand;
Ar is selected from the group consisting of:

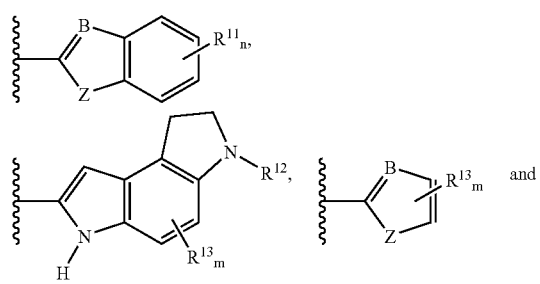

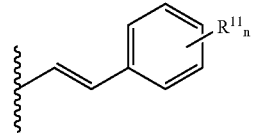

in which B is N or CR$^{10}$;
R$^{10}$ is selected from the group consisting of OH, C$_{1-4}$ alkoxy, C$_{1-4}$ alkyl, —NO$_2$, —NH$_2$, —CN, Cl, Br, I, —NHCOR$^{14}$, —COOH, —CONHR$^{15}$, —NHCOOR$^{15}$, —COOR$^{15}$ and H;
Z is selected from the group consisting of O, S, —CH=CH— and NH;
the or each R$^{11}$ is selected from the group consisting of OH, C$_{1-4}$ alkoxy, C$_{1-4}$ alkyl, —NO$_2$, —NH$_2$, —NHR$^{16}$, —NR$^{16}$$_2$, —N$^+$R$^{16}$$_3$, —CN, Cl, Br, I, —NHCOR$^{14}$, —COOH, —CONHR$^{15}$ —NHCOOR$^{15}$ and COOR$^{15}$;
n is an integer in the range 0 to 4;
R$^{12}$ is selected from the group consisting of H, —COAr$^1$, —CONH$_2$, —COOH, —COR$^{15}$ or —COOR$^{15}$;
the or each R$^{13}$ is selected from the group consisting of OH, C$_{1-4}$ alkoxy, C$_{1-4}$ alkyl, —NO$_2$, —NH$_2$, —NHR$^{16}$, —NR$^{16}$$_2$, —N$^+$R$^{16}$$_3$, —CN, Cl, Br, I, —NHCOR$^{14}$, —COOH, —CONHR$^{15}$, —NHCOOR$^{15}$ and —COOR$^{15}$;
m is 0, 1 or 2;
R$^{14}$ is selected from the group consisting of C$_{1-4}$ alkyl, optionally substituted phenyl, optionally substituted heteroaryl, C$_{7-12}$ aralkyl, Ar$^1$ and a ligand;
R$^{15}$ is selected from the group consisting of C$_{1-4}$ alkyl, optionally substituted phenyl, C$_{7-12}$-aralkyl and optionally substituted heteroaryl and a ligand;
the or each R$^{16}$ is independently selected from the group consisting of C$_{1-4}$ alkyl, optionally substituted phenyl, C$_{7-12}$-aralkyl and optionally substituted heteroaryl; and
Ar$^1$ is selected from the same groups as Ar;
provided that no more than one group R$^{11}$ or R$^{13}$ in any one ring includes a group Ar$^1$, and
a pharmaceutically acceptable excipient.

2. A method in which a compound of the formula

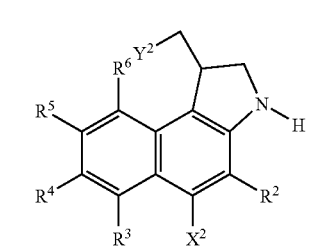

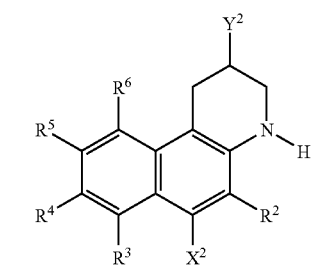

in which $R^2$, $R^3$, $R^4$, $R^5$ and $R^6$ are each independently selected from the group consisting of H, $C_{1-4}$ alkyl, —OH, $C_{1-4}$ alkoxy, —CN, Cl, Br, I, —$NO_2$, —$NH_2$, —$NHR^{16}$, —$NR^{16}{}_2$, —$N^+R^{16}{}_3$; —$NHCOR^8$, —COOH, —$CONHR^9$, —$NHCOOR^9$ and —$COOR^9$; $X^2$ is H; and
$Y^2$ is a leaving group or a hydroxyl or protected hydroxyl group; is reacted with a compound of the general formula IV $$R^{27}COY^3 \qquad\qquad IV$$

in which $R^{27}$ is selected from the group consisting of $C_{1-4}$-alkyl, optionally substituted phenyl, $C_{7-12}$-aralkyl, optionally substituted heteroaryl and $Ar^4$;
$Ar^4$ is selected from the group consisting of

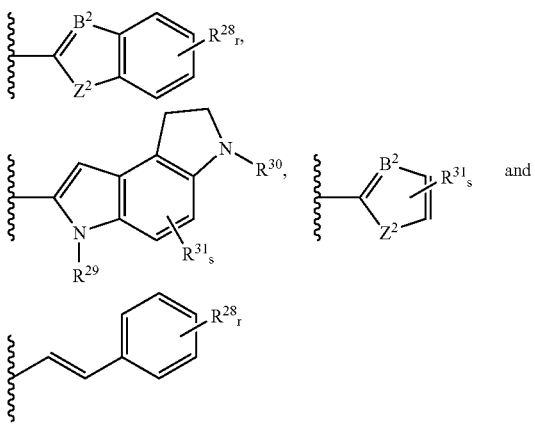

in which $B^2$ is N or $CR^{32}$;
$Z^2$ is selected from the group consisting of O, S, —CH=CH— and $NR^{33}$; the or each $R^{28}$ is selected from the group consisting of $C_{1-4}$-alkoxy, $C_{1-4}$-alkyl, $NO_2$, CN, Cl, Br, —$NHR^{33}$, —$NHR^{35}$, —$NR^{35}{}_2$, —$N^+R^{35}{}_3$—, —$NHCOR^{34}$, —COOH, —$CONHR^{36}$ and —$COOR^{36}$;
r is an integer in the range 0 to 4;
$R^{29}$ is an amine protecting group;
$R^{30}$ is selected from the group consisting of amine protecting groups, —$CONH_2$, —COOH, $COR^{36}$ and —$COAr^5$;
the or each $R^{31}$ is selected from the group consisting of $C_{1-4}$-alkoxy, $C_{1-4}$-alkyl, $NO_2$, CN, Cl, Br, —$NHR^{33}$, —$NHR^{35}$, —$NR^{35}{}_2$, —$N^+R^{35}{}_3$, I, —$NHCOR^{34}$, —COOH, —$CONHR^{36}$ and —$COOR^{35}$;
s is 0, 1 or 2;
$R^{32}$ is, selected from the group consisting of H $C_{1-4}$-alkoxy, $C_{1-4}$-alkyl, $NO_2$, CN, Cl, Br, I, —$NHR^{33}$, —$NHR^{35}$, —$NR^{35}{}_2$, —$N^+R^{35}{}_3$, —$NHCOR^{34}$, —COOH, —$CONHR^{36}$ and $COOR^{36}$;
$R^{33}$ is an amine protecting group;
$R^{34}$ is selected from the group consisting of $Ar^5$, $C_{1-4}$-alkyl, optionally substituted phenyl, $C_{7-12}$-aralkyl optionally substituted heteroaryl and a ligand;
$R^{35}$ is selected from the group consisting of $C_{1-4}$-alkyl, optionally substituted phenyl, $C_{7-12}$-aralkyl and optionally substituted heteroaryl;
$R^{36}$ is selected from the group consisting of $C_{1-4}$-alkyl, optionally substituted phenyl, $C_{7-12}$-aralkyl, optionally substituted heteroaryl and a ligand;

$Ar^5$ is selected from the same groups as $Ar^4$, and
$Y^3$ is a leaving group;
provided that no more than one $R^{28}$ or $R^{31}$ is any one ring is $NHCOAr^5$.

3. A method according to claim 2 which is carried out in the presence of an amide coupling reagent.

4. A method according to claim 2 in which the product is subsequently subjected to an amine deprotection step in which at least one $R^{29}$ or $R^{33}$ group is replaced by H.

5. A method according to claim 2 in which $Y^2$ is selected from the group consisting of —$OCOOR^{17}$, —$OCONHR^{18}$, Cl, Br, I, and —$OSOOR^{19}$, in which $R^{17}$, $R^{18}$ and $R^{19}$ are selected from the group consisting of $C_{1-4}$ alkyl, optionally substituted phenyl, $C_{7-12}$-aralkyl and optionally substituted heteroaryl.

6. A method according to claim 4 in which $Y^2$ is Cl.

7. A method according to claim 2 in which $Ar^5$ is selected from the group consisting of

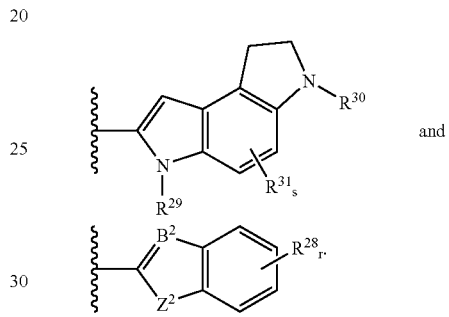

8. A method according to claim 2 in which $R^{27}$ is $Ar^4$.

9. A method according to claim 8 in which $Ar^4$ is a group

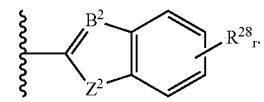

10. A method according to claim 9 in which, in $R^{27}$, r is at least 1 and one of the groups $R^{28}$ is —$NHCOAr^5$.

11. A method according to claim 10 in which $Ar^5$ is

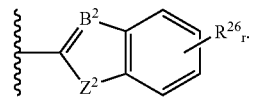

12. A method according to claim 8 in which $Ar^4$ is a group

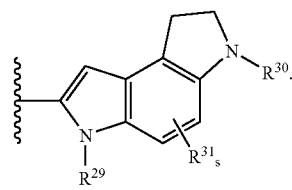

13. A method according to claim 12 in which $R^{30}$ is —$COAr^5$.

14. A method according to claim 13 in which, in $R^{27}$, $Ar^5$ is a group

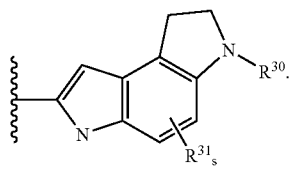

15. A method according to claim 2 in which the compound of the formula III is produced in a series of preliminary steps comprising a cyclisation step in which a compound of the general formula VI

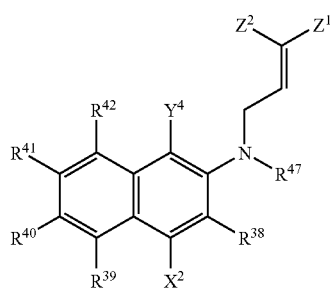

VI in which $R^{38}$ through $R^{42}$, $X^2$ and $Y^2$ are the same as in the compound of the formula III;
$R^{47}$ is an amine protecting group,
one of $Z^1$ and $Z^2$ is $Y^5$ and the other is H;
$Y^5$ is a leaving group which is different from or the same as $Y^2$ and
$Y^4$ is a radical leaving group;
is cyclised via an arylradical-alkene cyclisation step in the presence of a catalyst.

16. A method according to claim 15 in which $Z^1$ is $Y^2$ and in which the cyclisation step is carried out in the presence of a free radical to form a dihydropyrole ring.

17. A method according to claim 15 in which the free radical is generated from azoisobutyronitrile or is a 2,2,6,6-tetramethylpiperidinyloxy free radical.

18. A method according to claim 16 in which the catalyst is tributyl tin hydride.

19. A method according to claim 15 in which $Z^2$ is $Y^5$, $Y^5$ is a trialkyl tin radical, and the cyclisation step is carried out in the presence of a palladium complex to form a tetrahydroquinoline, which is oxidised to form an epoxide, the epoxide then being reduced to form an alcohol compound if $Y^2$ is other than hydroxyl, the hydroxyl group is subsequently converted into $Y^2$.

20. A method according to claim 14 in which $Y^4$ is a halogen.

21. A pharmaceutical composition according to claim 1 in which Y is selected from the group consisting of —OCOOR$^{17}$, —OCONHR$^{18}$, Cl, Br, I, and —OSOOR$^{19}$, in which $R^{17}$, $R^{18}$ and $R^{19}$ are each selected from the group consisting of $C_{1-4}$ alkyl, optionally substituted phenyl, $C_{7-12}$-aralkyl and optionally substituted heteroaryl.

22. A pharmaceutical composition according to claim 21 in which Y is Cl.

23. A pharmaceutical composition according to claim 22 in which $Ar^1$ is

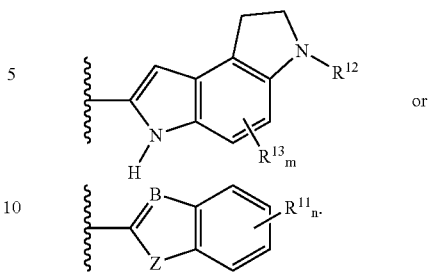

24. A pharmaceutical composition according to claim 1 in which $R^1$ is Ar.

25. A pharmaceutical composition according to claim 24 in which Ar is a group

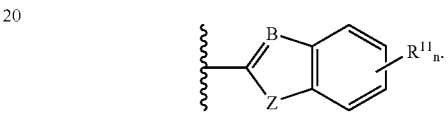

26. A pharmaceutical composition according to claim 25 in which n is at least 1 and one of the groups $R^{11}$ of the Ar group is —NHCOAr$^1$.

27. A pharmaceutical composition according to claim 26 in which $Ar^1$ is a group

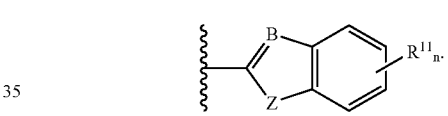

28. A pharmaceutical composition according to claim 27 in which, in $Ar^1$, either
i) n is at least 1 and $R^{11}$ is other than —NHCOAr$^1$, or
ii) n is 0.

29. A pharmaceutical composition according to claim 24 in which Ar is a group

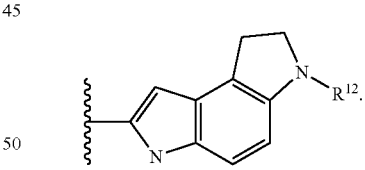

30. A pharmaceutical composition according to claim 29 in which $R^{12}$ is —COAr$^1$.

31. A pharmaceutical composition according to claim 30 in which $Ar^1$ is a group

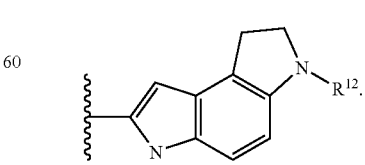

32. A pharmaceutical composition according to claim 31 in which, in $Ar^1$, $R^{12}$ is other than —COAr$^1$.

33. A pharmaceutical composition according to claim 1 in which $R^2$ is H.

34. A pharmaceutical composition according to claim 1 in which $R^3$ is H.

35. A pharmaceutical composition according to claim 1 in which $R^4$ is H.

36. A pharmaceutical composition according to claim 1 in which $R^5$ is H, $C_{1-4}$-alkoxy or —CN.

37. A pharmaceutical composition according to claim 36 in which $R^5$ is MeO or H.

38. A pharmaceutical composition according to claim 1 in which $R^6$ is H.

39. A compound of the general formula II or a salt thereof

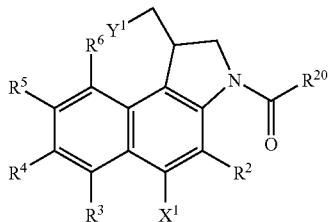

II in which $R^2$, $R^3$, $R^5$ and $R^6$ are each independently selected from the group consisting of H, $C_{1-4}$ alkyl, —OH, $C_{1-4}$ alkoxy, —CN, Cl, Br, I, —NO$_2$, —NH$_2$, —NHR$^{16}$, —NR$^{16}_2$, —N$^+$R$^{16}_3$; —NHCOR$^8$, —COOH, —CONHR$^9$, —NHCOOR$^9$ and —COOR$^9$;

$X^1$ is H;

$Y^1$ is a leaving group;

$R^{20}$ is $R^7$, $OR^7$, —NH$_2$ or Ar$^2$;

$R^7$ is selected from the group consisting of $C_{1-4}$ alkyl, optionally substituted phenyl, $C_{7-12}$-aralkyl, optionally substituted heteroaryl and a ligand;

Ar$^2$ is selected from the group consisting of

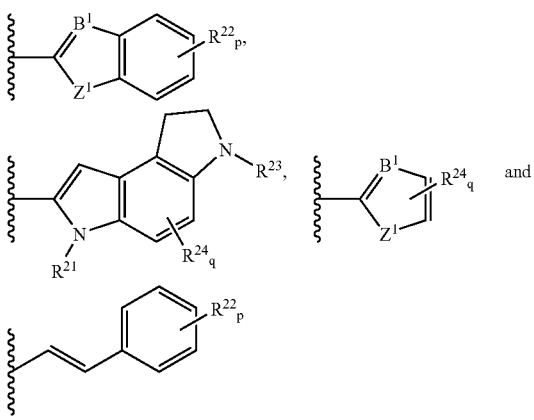

in which $B^1$ is N or $CR^{22}$;

$Z^1$ is selected from the group consisting of O, S, —CH=CH— or $NR^{21}$;

$R^{21}$ is H or an amine protecting group;

the or each $R^{22}$ is selected from the group consisting of OH, $C_{1-4}$ alkoxy $C_{1-4}$ alkyl, $NO_2$, —NHR$^{21}$, —NHR$^{26}$, —NR$^{26}_2$, —N$^+$R$^{26}_3$, —CN, Cl, Br, I, —NHCOR$^{25}$, —COOH, —CONHR$^7$ and —COOR$^7$;

p is an integer in the range 0 to 4;

$R^{23}$ is selected from the group consisting of H, COAr$^3$, —CONH$_2$, —COOH or —COR$^7$ or is an amine protecting group;

the or each $R^{24}$ is selected from the group consisting of OH, $C_{1-4}$ alkoxy $C_{1-4}$ alkyl, $NO_2$, —NHR$^{21}$, —NHR$^{26}$, —NR$^{26}_2$, —N$^+$R$^{26}_3$, —CN, Cl, Br, I, —NHCOR$^{25}$, —COOH, —CONHR$^7$ and —COOR$^7$;

q is 0, 1 or 2

$R^{25}$ is selected from the group consisting of $C_{1-4}$ alkyl, optionally substituted phenyl, optionally substituted heteroalkyl, $C_{7-12}$ aralkyl, Ar$^3$ and a ligand;

$R^{26}$ is selected from the group consisting of $C_{1-4}$ alkyl, optionally substituted phenyl, $C_{7-12}$-aralkyl and optionally substituted heteroaryl; and Ar$^3$ is selected from the same groups as Ar$^2$ provided that no more than one $R^{22}$ or $R^{24}$ in any one ring includes a group Ar$^3$.

40. A compound according to claim 39 in which $Y^1$ is selected from the group consisting of —OCOOR$^{17}$, —OCONHR$^{18}$, Cl, Br, I, and —OSOOR$^{19}$ in which $R^{17}$, $R^{18}$ and $R^{19}$ are selected from the group consisting of $C_{1-4}$ alkyl, optionally substituted phenyl, $C_{7-12}$-aralkyl and optionally substituted heteroaryl.

41. A compound according to claim 40 in which Y is Cl.

42. A compound according to claim 39 in which Ar$^3$ is

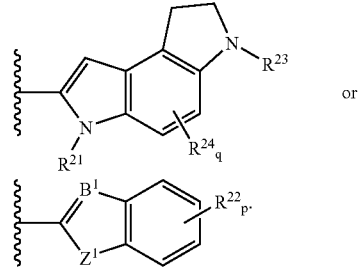

or

43. A compound according to claim 39 in which $R^{20}$ is Ar$^2$.

44. A compound according to claim 43 in which Ar$^2$ is a group

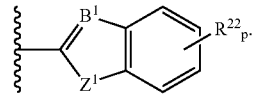

45. A compound according to claim 44 in which p is at least 1 and one of the groups $R^{22}$ of the group $R^{20}$ is a group —NHCOAr$^3$.

46. A compound according to claim 45 in which Ar$^3$ is

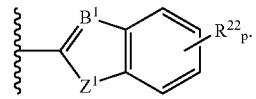

47. A compound according to claim 46 in which, in Ar$^3$, either i) p is at least 1 and $R^{22}$ is other than —NHCOAr$^3$, or ii) p is 0.

48. A compound according to claim 43 in which Ar$^2$ is a group

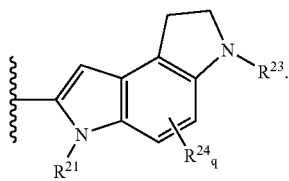

49. A compound according to claim 48 in which $R^{23}$ is COAr³.

50. A compound according to claim 49 in which Ar³ is

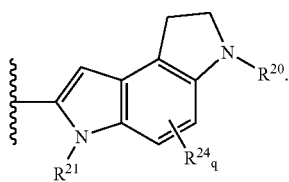

51. A compound according to claim 42 in which, in Ar³, $R^{23}$ is other than —COAr³.

52. A compound according to claim 39 in which $R^{20}$ is other than Ar².

53. A compound according to claim 39 in which $R^2$ is H.

54. A compound according to claim 39 in which $R^3$ is H.

55. A compound according to claim 39 in which $R^4$ is H.

56. A compound according to claim 39 in which $R^5$ is selected from the group consisting of H, $C_{1-4}$-alkoxy and —CN.

57. A compound according to claim 56 in which $R^5$ is MeO.

58. A compound according to claim 39 in which $R^6$ is H.

59. A compound according to claim 39 selected from the group consisting of:

3-(tert-Butyloxycarbonyl)-1-(chloromethyl)-1,2-dihydro-3H-benz[e]indole; and 1-(chloromethyl)-3-[(5-methoxyindol-2-yl )carbonyl]-1,2-dihydro-3H-benz[e]indole.

* * * * *